United States Patent [19]

Cook et al.

[11] Patent Number: 5,656,282
[45] Date of Patent: Aug. 12, 1997

[54] PACKAGE FOR CONTAINING AND APPLYING A BUG REPELLENT PATCH

[75] Inventors: Charles D. Cook, Fairfield; Nicholas A. Ahr, Cincinnati; Charles J. Berg, Wyoming; Michael E. Hilton, Cincinnati, all of Ohio

[73] Assignee: The Procter & Gamble Company, Cincinnati, Ohio

[21] Appl. No.: 369,068

[22] Filed: Jan. 5, 1995

[51] Int. Cl.$^6$ .................................................. A01N 25/08
[52] U.S. Cl. ............................. 424/409; 424/408; 424/412
[58] Field of Search ............................... 424/408, 412, 424/409

[56] References Cited

U.S. PATENT DOCUMENTS

| | | | |
|---|---|---|---|
| 2,402,982 | 7/1946 | Steenbergen | 206/63.2 |
| 3,018,881 | 1/1962 | Wall | 206/56 |
| 3,295,246 | 1/1967 | Landsman et al. | 43/131 |
| 3,858,807 | 1/1975 | Rabussier et al. | 239/56 |
| 4,131,195 | 12/1978 | Worrell, Sr. | 206/205 |
| 4,168,000 | 9/1979 | MacRitchie | 206/63.3 |
| 4,264,008 | 4/1981 | Kozlow | 206/441 |
| 4,285,468 | 8/1981 | Hyman | 239/55 |
| 4,781,293 | 11/1988 | Johns | 206/441 |
| 4,804,142 | 2/1989 | Riley | 239/56 |
| 4,881,671 | 11/1989 | Horton et al. | 224/222 |
| 4,917,929 | 4/1990 | Heincke | 428/41 |
| 4,923,745 | 5/1990 | Wolfert et al. | 428/35.4 |
| 4,932,155 | 6/1990 | Friemel et al. | 43/125 |
| 5,003,635 | 4/1991 | Peterson | 2/69 |
| 5,033,122 | 7/1991 | Smith | 2/209.3 |
| 5,071,704 | 12/1991 | Fischel-Ghodsian | 428/354 |
| 5,333,753 | 8/1994 | Etheredge | 221/33 |

*Primary Examiner*—D. Gabrielle Phelan
*Attorney, Agent, or Firm*—Ronald W. Kock

[57] ABSTRACT

A pouch package, containing a volatile solution-impregnated patch, is made of a peelable barrier film. The pouch envelops an absorbent substrate saturated preferably with bug repellent fluid. A PSA (pressure sensitive adhesive) coated backing film is laminated to the absorbent substrate. The backing film has a connecting portion which is peelably sealed to the inside of the pouch. When the pouch is peeled open, the PSA coated backing film is exposed and placed against a target surface, such as a patch wearer's clothing. Finally, the side of the pouch facing the absorbent substrate is peeled off the backing film connecting portion to expose the absorbent substrate. A key to functionality of the pouch package is differential adhesion. First, the pouch barrier film must be peelable from itself, yet it must not adhere to the pressure sensitive adhesive on the backing film. A release paper may be used to cover the PSA when peeling the pouch open. Second, the pouch film must be peelable from the backing film connecting portion without disturbing the bond between the fastening surface and the target surface. Third, the backing film must be laminated to the absorbent substrate more strongly than the PSA adheres to the backing film, so that when the patch is removed from the target surface, the PSA stays with the patch.

6 Claims, 3 Drawing Sheets

U.S. Patent   Aug. 12, 1997   Sheet 1 of 3   5,656,282
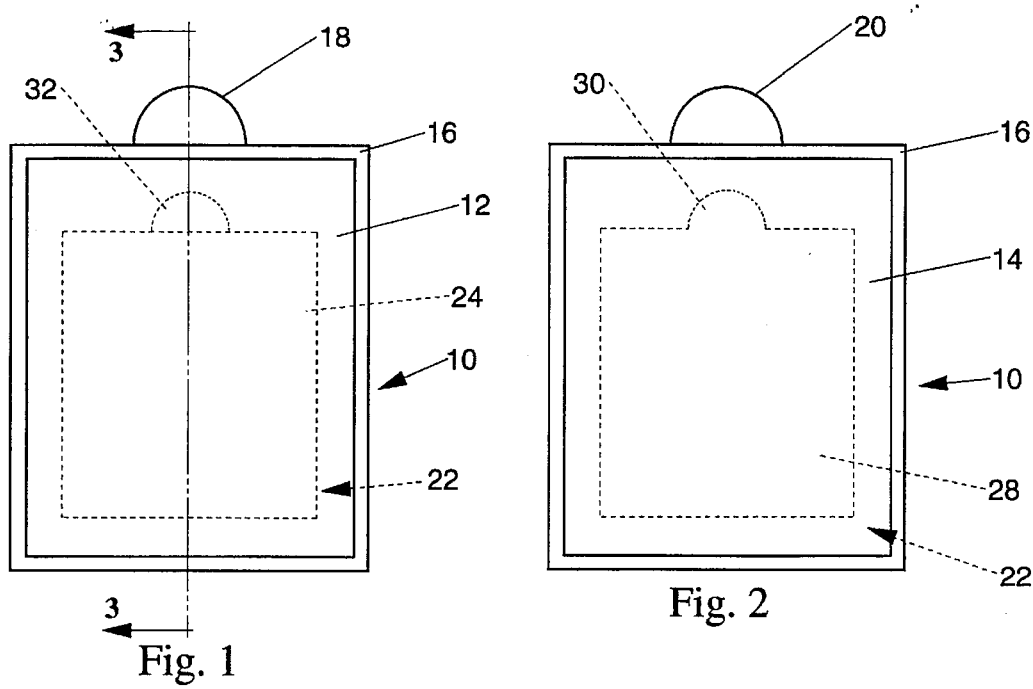
Fig. 1
Fig. 2
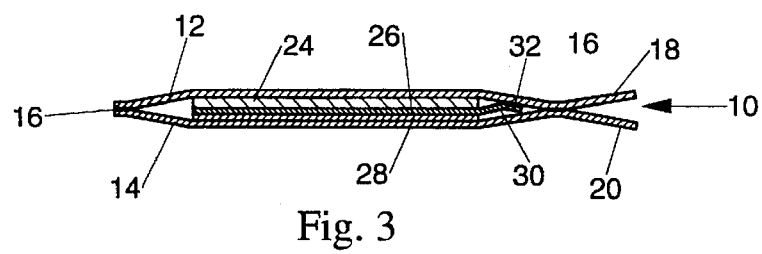
Fig. 3
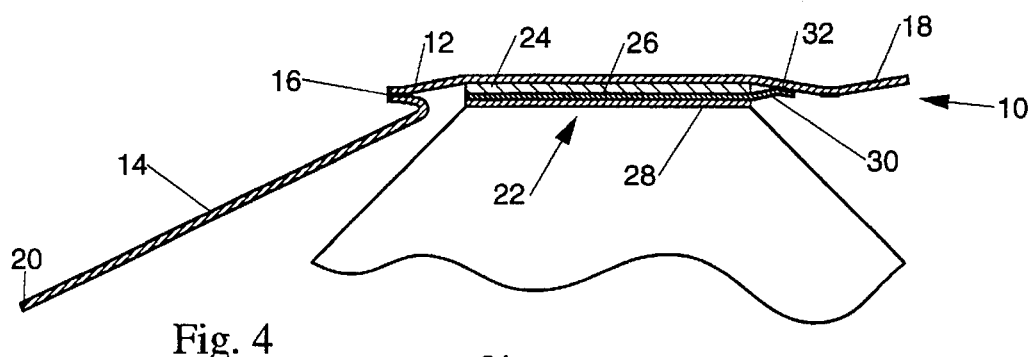
Fig. 4
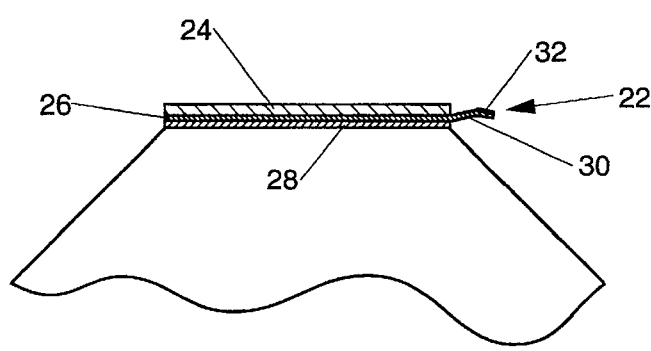
Fig. 5

5,656,282

PACKAGE FOR CONTAINING AND APPLYING A BUG REPELLENT PATCH

FIELD OF THE INVENTION

The present invention relates to pouch type packages which contain volatile substances, and more particularly to such packages wherein volatile substances are potentially irritating and are contained in a patch attachable to a user's clothing or limbs. The present invention also relates to packages which enable a user to apply the contents of the package to a target surface without having to contact the contents.

BACKGROUND OF THE INVENTION

Bug or insect repellent for personal use has been historically delivered in a number of different ways. For example, it may be sprayed onto one's skin, sprayed into one's immediate environment, and/or sprayed onto one's clothing. The bug repellent solution is typically volatile so that vapors are emitted which encourage bugs to stay away from one's body.

Longevity of protection for a bug repellent delivered in this manner has always been a problem, however. More recently, absorbent substrates saturated with volatile solutions of bug repellent, made in the form of patches, have been available for application to clothing. When such patches have a barrier material between the substrate and a target surface, such as the user's clothing, greater volumes of solution may be safely used. As a result, such patches may be designed to provide a longer lasting bug repellent.

Any patch containing a volatile solution must be contained in a package which offers a barrier to vaporization of the solution prior to application of the patch. Peelable packages made of barrier films are well known in the art for this purpose. Besides the function of containing the volatile solution prior to use, we have discovered another important consideration for a bug repellent patch package. That is, application of the patch to a target surface should not involve direct user contact with the substrate or solution because of the potentially irritating effect of the solution. Chemicals may be absorbed into one's skin or transferred from a finger surface into one's mouth or eyes, for example, if one touches such a patch.

What has been missing is a package for containing a potentially irritating solution-impregnated patch, such as for bug repellents, which enables the user to apply the patch to a target surface without contacting the patch.

SUMMARY OF THE INVENTION

In one aspect of the present invention, a package is suitable for containing a volatile substance-impregnated substrate and for enabling a user to apply the substrate to a target without contacting the substrate. Such a package comprises an impermeable barrier film pouch enclosing the substrate. The pouch has a top film, a bottom film, and a peelable seal between the top film and the bottom film to seal the pouch in an air-tight manner. The top film and the bottom fill each have an unsealed opening tab extending beyond the peelable seal, and each opening tab is positioned so that the pouch may be opened by pulling apart the opening tabs. The substrate is connected to the pouch such that when the pouch is peeled open, the substrate position remains controllable by manipulation of the pouch. The package also comprises a means for connecting the substrate to the target. For example, a fastening means on an outer surface of the pouch adjacent the opening tabs permits peeling open the pouch to expose the substrate, folding the bottom film approximately 360°, and attaching the bottom film to the top film to form a loop attachable around a user's limb or parts of clothing such as a belt loop.

Another means for connecting the substrate to the target is an impermeable backing film laminated to the substrate to form a patch. The backing film has a substrate side, a fastening surface opposite the substrate side, and a connecting portion extending beyond the periphery of the patch. The connecting portion is peelably attached to the pouch. The fastening surface has an attachment means which is exposed for attachment to the target when the bottom film is peeled away from the top fill. The attachment means is either pressure sensitive adhesive or a hook-like material system. A hook-like material system comprises one surface having a plurality of hook-like engaging elements which matingly engage with a second surface having a fibrous engagement surface. If the attachment means is pressure sensitive adhesive, it may have a release paper covering it so that the adhesive does not interfere with peeling the bottom fill away from the top film.

An alternative construction of a pouch of the present invention has a substrate attached to an inner surface of the bottom film. On the outer surface of the bottom film is a means for connecting the pouch to a target surface. Once the pouch is attached to the target surface, the top film of the pouch is peeled off the bottom fill to expose the substrate. After the top film is removed, the bottom film of the pouch and the substrate form a patch, which is attached to the target surface.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

FIG. 1 is a top plan view of a package for containing and applying a bug repellent patch of the present invention, disclosing a pouch having peelable border and a volatile-containing substrate contained therein;

FIG. 2 is a bottom plan view thereof, disclosing the pouch having a peelable border, showing a barrier material on the opposite side of the substrate, the barrier material having a fastening surface on the side of the barrier material opposite the substrate;

FIG. 3 is a side elevation cross-section view thereof, taken along section line 3—3 of FIG. 1, showing the stackup of laminates of the pouch and the patch of the present invention.

FIG. 4 is another side elevation cross-section view thereof, similar to FIG. 3, except that it shows the pouch peeled open to expose the patch;

FIG. 5 is yet another side elevation cross-section view thereof, similar to FIG. 3, disclosing the pouch removed from the patch, and the patch applied to a target surface;

FIG. 12 is a side elevation cross-section view thereof, taken along section line 12—12 of FIG. 10, showing the stackup of layers of the pouch of the present invention.

DETAILED DESCRIPTION OF THE INVENTION

Figure 6:
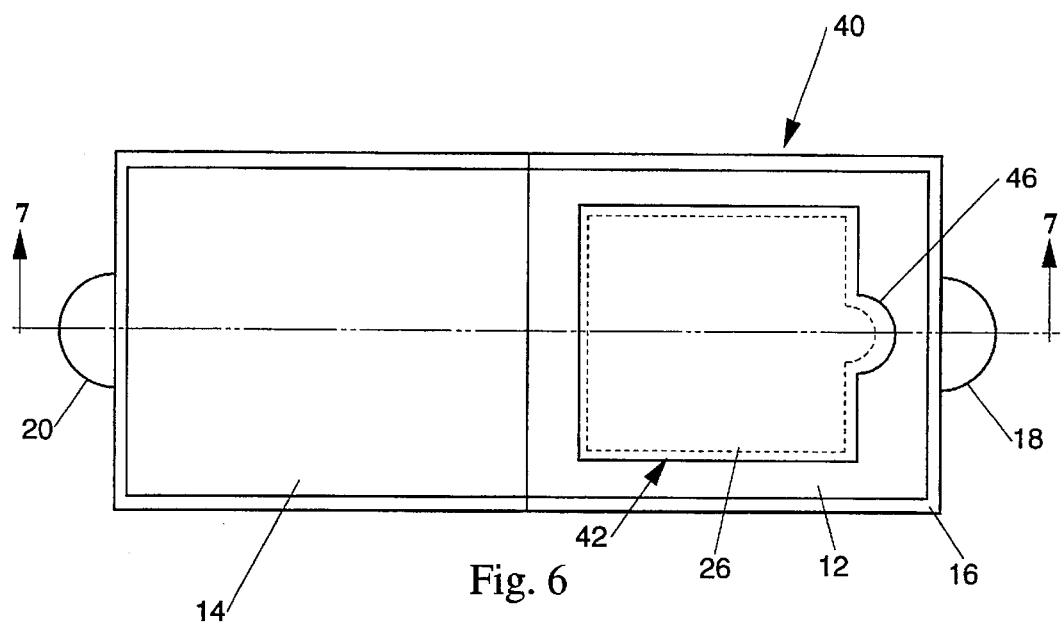
FIG. 6 is a bottom plan view of an alternative package of the present invention, showing a peeled open pouch which exposes a patch having an attachment adhesive covered by a release paper.

Referring now to the drawings, and more particularly to FIGS. 1 and 2, there is shown a preferred embodiment of the present invention, which is a package for containing and applying a bug repellent patch, and is generally indicated as 10. Package 10 is a vapor impermeable barrier pouch which has a top barrier film 12 and a bottom barrier film 14 which are sealed together at their perimeter to form a peelable seal 16. Peelable seal 16 seals pouch 10 closed in an air-tight manner to contain any volatile materials placed therein.

Top film 12 and bottom film 14 may also be made of one piece of barrier film folded in half along one perimeter edge of pouch 10. Both top film 12 and bottom film 14 have opening tabs 18 and 20, respectively, extending beyond perimeter seal 16 to provide finger gripping surfaces enabling one to peel open pouch 10. Both opening tabs 18 and 20 extend from the same side of pouch 10 either overlapping or slightly offset such that a user may easily separate them for gripping purposes. Such a tab may include an entire edge of top film 12 or bottom film 14. If top film 12 and bottom film 14 are formed from a single piece of film folded in half, opening tabs 18 and 20 preferably extend from the side opposite the fold.

Pouch 10 contains a patch 22, which is a laminate including an absorbent substrate 24 saturated with a volatile solution such as bug repellent fluid, and an impermeable backing film 26 laminated to absorbent substrate 24. On the opposite side of backing film 26 from substrate 24 is a fastening surface 28, which may be a hook-like material or a PSA (pressure sensitive adhesive) coating, for example. Backing film 26 has a connecting portion 30 extending beyond the perimeter of substrate 24. Connecting portion 30 is peelably fastened to an inside surface 34 of top film 12 at joint 32. Joint 32 may be a light fusion seal, or a PSA seal via a coating of PSA on the same side of connecting portion 30 as substrate 24.

When pouch 10 is peeled open, fastening surface 28 on backing film 26 is exposed. Patch 22 may be placed against a target surface, such as a wearer's clothing or skin, by gripping only opening tabs 18 and 20 of pouch 10 and pressing against the outside of top film 12 in order to avoid contacting patch 22. Joint 32 holds backing film connecting portion 30 to pouch 10 so that the position of patch 22 may be controlled without contacting patch 22. Once patch 22 is oriented and fastening surface 28 on backing film 26 is placed against the target, top film 12 of pouch 10 may be peeled off connecting portion 30 to expose absorbent substrate 24. After removal, pouch 10 is discarded. Backing film 26 serves as a barrier between substrate 24, saturated with bug repellent fluid, and the user's clothing or skin so that no bug repellent fluid reaches the clothing or skin.

Figure 7:
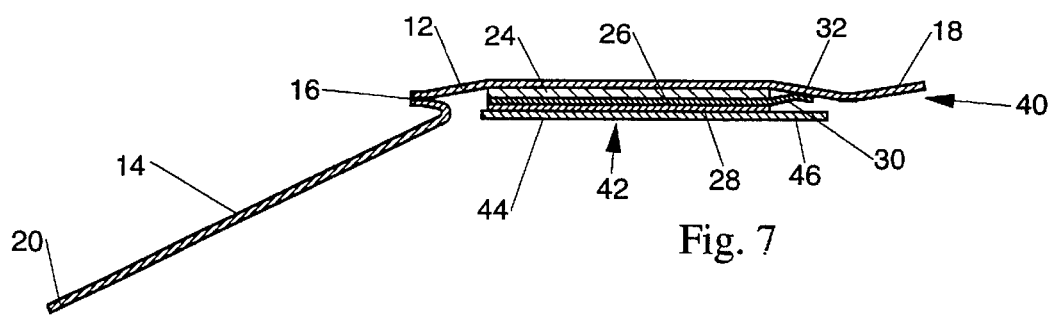
FIG. 7 is a side elevation cross-section view thereof, taken along section line 7—7 of FIG. 6, showing a stackup of laminates of the pouch and the patch of the present invention.

A key to functionality of this package is differential adhesion. First, top film 12 and bottom film 14 of pouch 10 are preferably peelable from each other in order to conveniently open the package. However, bottom film 14 should not adhere to fastening surface 28 on backing film 26. This differential adhesion can be achieved by using peelable film such as Zeelon 244, a product of James River Corporation, and made in Greensburg, Ind. Zeelon 244 is a 1.6 mil thick, coextruded HDPE/EVA blend blown film. Fastening surface 28 would not stick to bottom film 14 if it were a hook-like material, or if it were PSA covered by a release paper, as shown in FIG. 7. However, fastening surface 28 is preferably a PSA coating, such as specification no. 405-4, made by Century Adhesives Corp. of Columbus, Ohio. With the latter PSA, bottom film 14 acts as a release paper.

Second, backing film connecting portion 30 has joint 32 which is preferably peelable from top film 12 without disturbing the bond formed by fastening surface 28 and the target surface. This differential adhesion is achieved by sizing joint 32 to be much narrower than the bond with the target surface, in the direction of peeling off the pouch, and by using a peelable bond. For example, backing film 26 may also be Zeelon 244, lightly fused to the inner surface 34 of top film 12. Alternatively, joint 32 may have a PSA which adheres to top film 12, such as specification no. 405-4, made by Century Adhesives Corp. of Columbus, Ohio.

Third, backing film 26 is preferably laminated to absorbent substrate 24 more strongly than fastening surface 28 adheres to the target surface, and fastening surface 28 should adhere to backing film 26 more aggressively than to the target surface, so that when patch 22 is removed from the target surface, the substrate and fastening surface 28 both stay with backing film 26. Removal of patch 22 from a target surface is accomplished without touching substrate 24 by lifting connecting portion 30 of backing film 26.

A strongly bonded laminate is achieved by the selection of substrate 24 and the method of laminating backing film 26 to substrate 24, and by the method of attaching fastening surface 28 to backing film 26. For example, substrate 24 may be a nonwoven thermoplastic material which is spot melted to a thermoplastic backing film by a heated tool. Alternatively, substrate 24 may be a cellulose fiber material, a sponge material, or a foam material, which is laminated by hot melt adhesive or a highly aggressive PSA to backing film 26.

Fastening surface 28 may be attached to backing film 26 at the same time substrate 24 is laminated to it, or fastening surface 28 may be attached separately. If a PSA, fastening surface 28 may be coated onto backing film 26. If a hook-like material, such material typically has its own engagement material, which may be laminated to backing film 26 by commonly used thermobonding techniques of hot melt adhesives, ultrasonic, radio frequency, or hot bar sealing. Alternatively, an aggressive pressure sensitive adhesive may be used.

In a particularly preferred embodiment of the present invention, top film 12 and bottom film 14 are made of Zeelon 244. Peelable seal 16 is achieved by impulse sealing, using a Vertrod thermal impulse sealer, made by Vertrod Corporation of Brooklyn, N.Y. Backing film 26 is preferably 1 mil thick surlyn, available from James River Corp. of Cincinnati, Ohio. It is laminated to a substrate made of Reverse CPN Paper, a material produced by The Procter & Gamble Company of Cincinnati, Ohio. Substrate 24 is preferably 2 inches (51 mm) by 2.5 inches (64 mm), and is 0.1 inches (2.5 mm) thick. It holds approximately two milliliters of fluid when saturated.

The lamination of substrate 24 to backing film 26 is achieved by pressure sensitive adhesive. The lamination PSA has specification no. H2031. It is made by Findley Adhesives of Wauwatosa, Wis. Fastening surface 28 is preferably a PSA coating about 1 mil thick, and has specification no. 405-4, which is not as aggressive as the lamination PSA. It is made by Century Adhesives Corp. of Columbus, Ohio. Joint 32 is preferably also a PSA seal using the 405-4 adhesive.

FIGS. 6 and 7 show an alternative embodiment of the package of the present invention, designated as 40. Package 40 is a pouch containing a patch. Pouch 40 has the same construction as pouch 10, except that it contains a patch 42, which is different from patch 22 only in that patch 42 includes a release paper 44 covering fastening surface 28. FIGS. 6 and 7 show pouch 40 already peeled open to expose the patch laminate.

Figure 8:
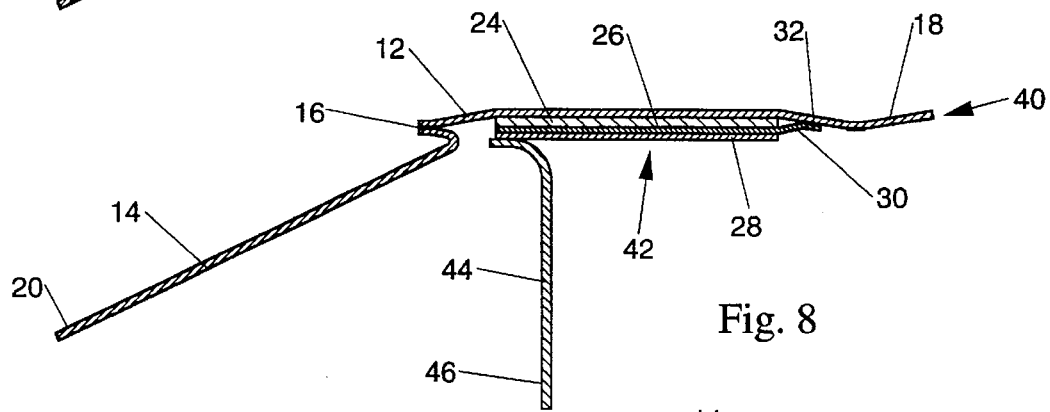
FIG. 8 is a side elevation cross-section view thereof, similar to FIG. 7, showing the release paper partially removed from the attachment adhesive for patch application to a target surface.

Fastening surface 28 is preferably a PSA which sticks to bottom film 14 of pouch 40 if left uncovered. Therefore, release paper 44 prevents such sticking, which would interfere with peeling open pouch 40. Release paper 44 has a removal tab 46 which enables the user to lift one end of release paper 44 and peel it off PSA 28 as shown in FIG. 8.

In a particularly preferred embodiment, release paper is a 25 pound basis weight paper, made by Akrosil of Appleton, Wis. Release paper 44 is placed onto PSA coating 28 after the coating is applied to backing film 26. When release paper 44 is removed, it is discarded along with pouch 40 once patch 42 is applied to its target surface.

Figure 9:
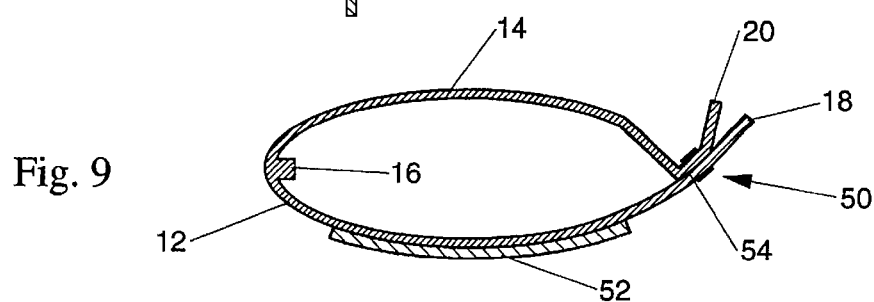
FIG. 9 is a side elevation cross-section view of another alternative package of the present invention, showing the pouch folded into a loop configuration, wherein the pouch remains connected to the patch during use.

FIG. 9 shows another embodiment of the package of the present invention, designated as 50. Package 50 is a pouch which contains a volatile solution-impregnated substrate which is laminated to the pouch instead of to a backing film. Pouch 50 is the same as pouch 10 and pouch 40 except that it contains only a substrate 52. Substrate 52 is preferably laminated to inner surface 34 of top film 12 by commonly used thermobonding techniques of hot melt adhesives, ultrasonic, radio frequency, or hot bar sealing. Alternatively, an aggressive pressure sensitive adhesive may be used. Substrate 52 is preferably the same material and size as substrate 24. The target for substrate 52 is the user's wrist or ankle or part of the user's clothing, such as a belt loop.

The embodiment of FIG. 9 is different from the other embodiments in that pouch 50 is used as a wrist-band or ankle-band. With substrate 52 attached to the barrier pouch film material, merely peeling open pouch 50 and folding bottom film 14 approximately 360° back on itself exposes substrate 52. There is no attachment of the substrate to one's clothing. Instead the loop formed by pouch 50 is used to hold the patch to a user's limb, such as a wrist or ankle. A fastening means 54, such as a stripe of adhesive or a hook-like material fastening system, located on top film 12 and/or bottom film 14 adjacent opening tabs 18 and 20, and opposite peelable bond 16, acts to hold the loop together. Opening tabs 18 and 20 may later be used to open the loop.

As with embodiments described herebefore, the user need not contact substrate 52 in order to peel open pouch 50 by opening tabs 18 and 20 and to loop pouch 50 around one's wrist or ankle and to connect the ends of pouch 50 together at adhesive stripe 54.

Figure 10:
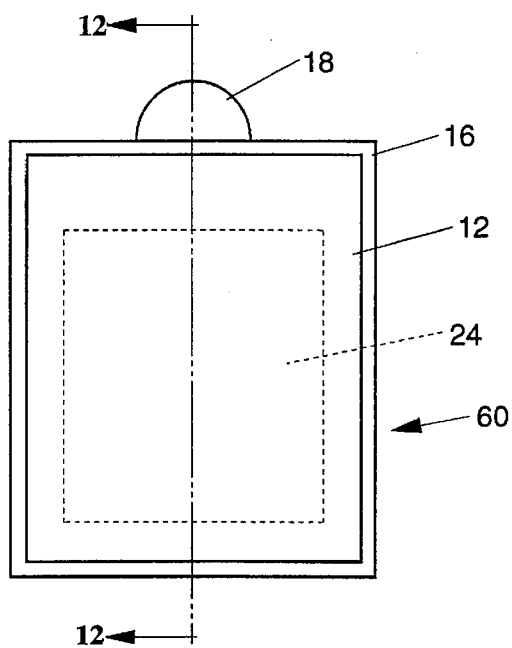
FIG. 10 is a top plan view of another alternative package for containing and applying a bug repellent patch of the present invention, disclosing a pouch having a peelable border and a volatile-containing substrate contained therein.
Figure 11:
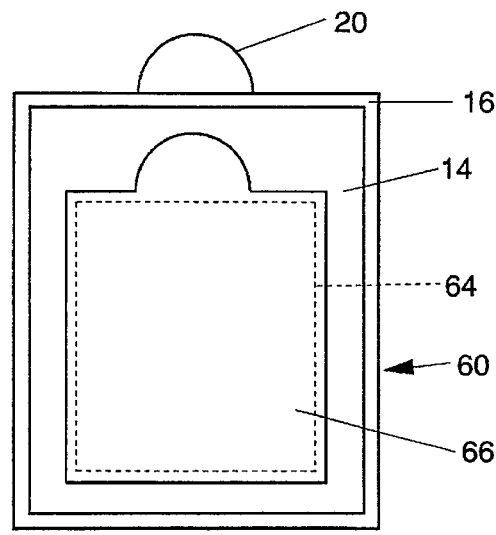
FIG. 11 is a bottom plan view thereof, disclosing the pouch having a peelable border, showing a release paper covering an adhesive coating on the outside of the pouch.
Figure 13:
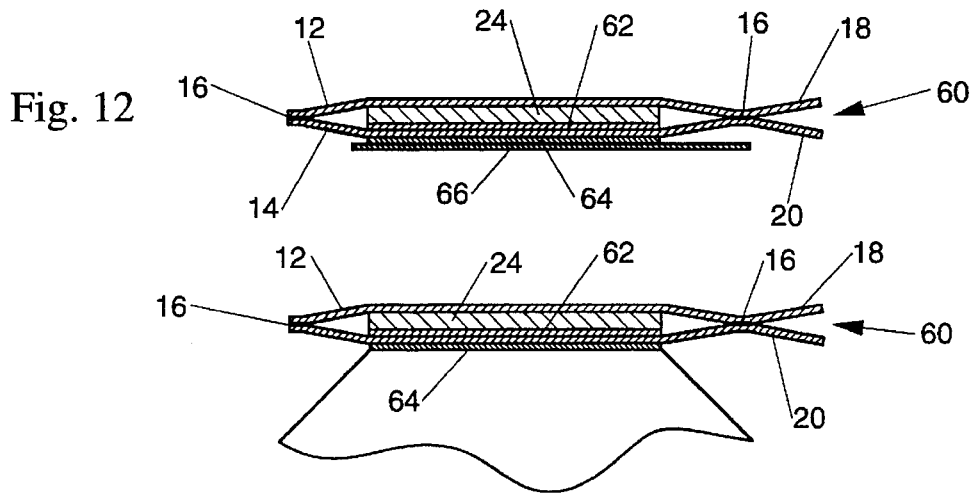
FIG. 13 is another side elevation cross-section view thereof, similar to FIG. 12, except that it shows release paper peeled off the adhesive coating to fasten the pouch to a target surface.

FIGS. 10 and 11 show still another embodiment of the present invention, designated as 60. Package 60, like package 10 is a pouch, which has top film 12, bottom film 14, peelable seal 16, opening tabs 18 and 20, and substrate 24 located therein. Substrate 24 is connected to bottom film 14, however, by PSA coating 62. Opposite PSA coating 62 on the outer surface of bottom fill 14 is connecting means 64, which may be Velcro-like hook material or anther PSA coating. If connecting means 64 is a PSA coating, as shown in FIGS. 11-14, a release paper 66 is attached to it, as shown in FIG. 12. Release paper 66 is removed and discarded before positioning pouch 60 against a target surface, as shown in FIG. 13.

Figure 14:
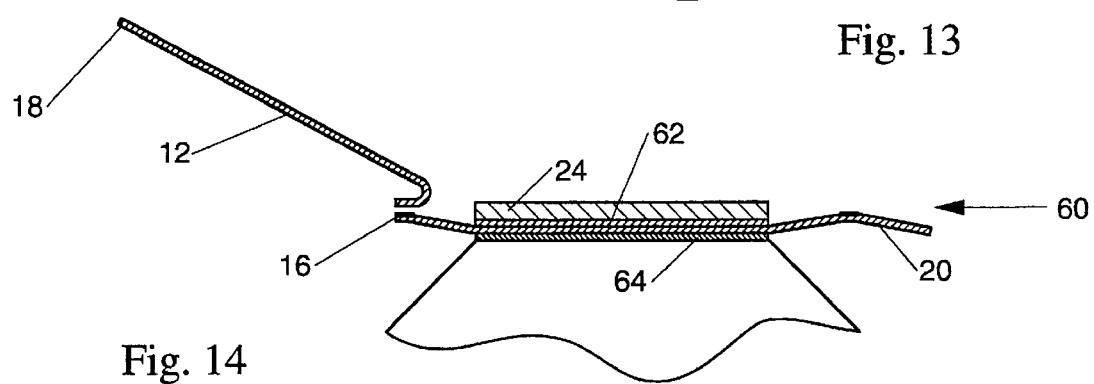
FIG. 14 is yet another side elevation cross-section view thereof, similar to FIG. 12, disclosing the top film of the pouch removed from the bottom film of the pouch to expose the substrate.

FIG. 14 shows that after pouch 60 is attached to a target surface, such as a user's clothing, top film 12 is peeled off bottom film 14 to expose the substrate. In this construction, differential adhesion is important. That is, connecting means 64 should provide a stronger bond than peelable seal 16, so that top film 12 may be removed without pulling the pouch off the target surface. Also, connecting means 64 should adhere to bottom film 14 more readily than to the target surface, so that removal of the patch by lifting opening tab 20 results in the removal of connecting means 64 as well as substrate 24.

Although any volatile solution may be used to impregnate substrate 24, a bug repellent is the intended solution of the present invention. Solutions such as those containing citronella are effective bug repellents.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A package containing a bug repellant-impregnated substrate and enabling a user to apply said substrate to a target without contacting said substrate, said package comprising:

a) an impermeable barrier film pouch enclosing said substrate, said pouch having a top film, a bottom film, and a peelable seal between said top film and said bottom film to seal said pouch in an air-tight manner, said pouch having opening tabs, said substrate being connected to said pouch such that when said pouch is peeled open, said substrate may be positioned by manipulating said pouch; and b) an impermeable backing film laminated to said substrate, said backing film having a fastening surface opposite said substrate, and a connecting portion being peelably attached to said pouch, said fastening surface being exposed for attachment to said target when said bottom film is peeled away from said top film.

2. A package containing a bug repellant-impregnated substrate and enabling a user to apply said substrate to a target surface without contacting said substrate, said package comprising:

a) an impermeable backing film laminated to said substrate, said backing film having a fastening surface opposite said substrate and a connecting portion; and b) an impermeable film pouch enclosing said patch, said pouch having a top film, a bottom film, and a peelable seal between said top film and said bottom film to seal said pouch in an air-tight manner, said top film and said bottom film each having an opening tab, each opening tab being positioned so that said pouch may be opened by pulling said opening tabs apart, said top film having an inner surface which is peelably sealed to said connecting portion of said backing film such that when said pouch is peeled open to expose said fastening surface, said connecting portion remains attached to said inner surface of said top film, said fastening surface being more strongly attracted to said backing film than to said bottom film, so that said pouch may be peeled open without interference from said fastening surface.

3. The package of claim 2 wherein said fastening surface adheres to said backing film and to said target surface more strongly than said connecting portion of said backing film adheres to said inner surface of said top film, so that said pouch may be removed from said connecting tab without pulling said patch off said target surface.

4. The package of claim 2 wherein said fastening surface adheres more strongly to said backing film than to said target surface, so that when said patch is removed from said target surface, said fastening surface remains on said backing film.

5. A package containing a bug repellant-impregnated substrate and enabling a user to apply said substrate to a target surface without contacting said substrate, said package comprising an impermeable film pouch enclosing said substrate, said pouch having a top film, a bottom film, and a peelable seal between said top film and said bottom film to seal said pouch in an air-tight manner, said top film and said bottom film each having an unsealed opening tab extending beyond said peelable seal, said opening tabs being positioned so that said pouch may be opened by pulling said opening tabs apart, said bottom film of said pouch being laminated to said substrate; said bottom film having a fastening surface opposite said substrate, said fastening surface having an adhesive for attachment to said target, said adhesive having a stronger bond than said peelable seal, so that said top film may be removed from said bottom film without pulling said pouch off said target surface.

6. The package of claim 5 wherein said attachment means adheres to said bottom film more readily than to said target surface, so that removal of said bottom film by lifting said opening tab also removes said attachment means.

* * * * *